United States Patent [19]

Anderson et al.

[11] 4,201,874
[45] May 6, 1980

[54] 3-ISOPROPENYL-6-HEPTENOIC ACID

[75] Inventors: Richard J. Anderson; Clive A. Henrick, both of Palo Alto, Calif.

[73] Assignee: Zoecon Corporation, Palo Alto, Calif.

[21] Appl. No.: 963,548

[22] Filed: Nov. 24, 1978

Related U.S. Application Data

[62] Division of Ser. No. 886,324, Mar. 13, 1978.

[51] Int. Cl.$^2$ .............................................. C07C 57/02
[52] U.S. Cl. ................................... 562/598; 562/401; 568/840
[58] Field of Search ................................ 562/598, 401

[56] References Cited

U.S. PATENT DOCUMENTS 3,998,873  12/1976  Hall et al. ............................ 562/598

OTHER PUBLICATIONS

Chemical Abstracts I, vol. 78 (1973), 135585a.
Chemical Abstracts II, vol. 85, (1976), 32383y.

Primary Examiner—Joseph E. Evans
Assistant Examiner—Vera C. Clarke
Attorney, Agent, or Firm—Donald W. Erickson

[57] ABSTRACT

Synthesis and intermediates for making insect pheromone useful in the control of red scale, *Aonidiella aurantii*.

2 Claims, No Drawings

3-ISOPROPENYL-6-HEPTENOIC ACID

This is a division, of application Ser. No. 886,324, filed Mar. 13, 1978.

This invention relates to the synthesis of a component of the sex pheromone of the California red scale, *Aonidiella aurantii* (Maskell) and intermediates therefor.

The California red scale is a pest of citrus. The natural female pheromone attracting the male red scale consists of 3-methyl-6-isopropenyl-9-decen-1-yl acetate (AI) and (z)-3-methyl-6-isopropenyl-3,9-decadien-1-yl acetate (AII). Roelofs et al., Nature 267, 698 (June 23, 1977).

The synthesis of the present invention can be outlined as follows:

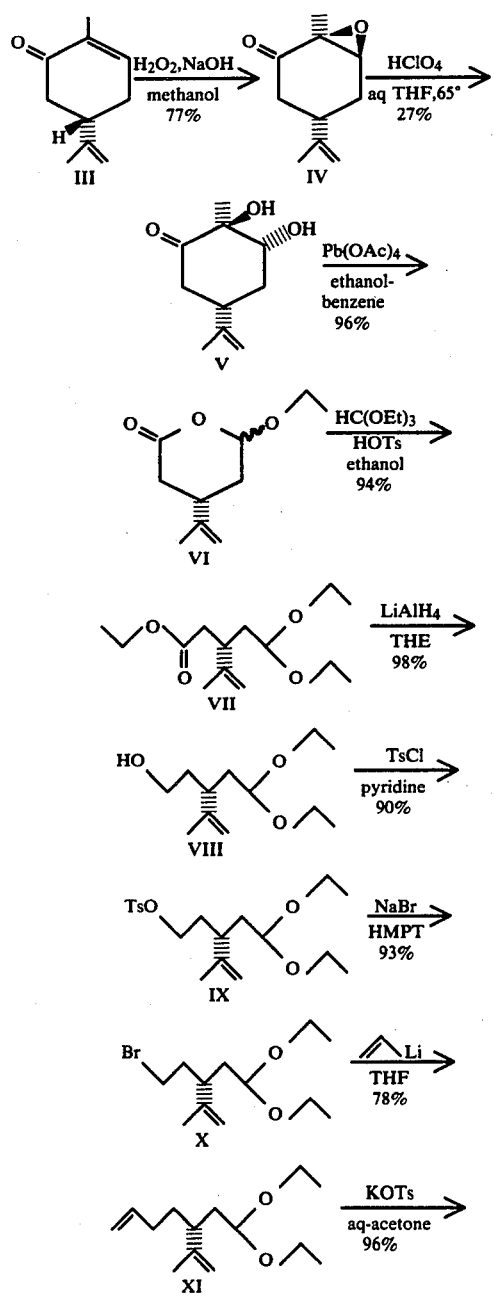

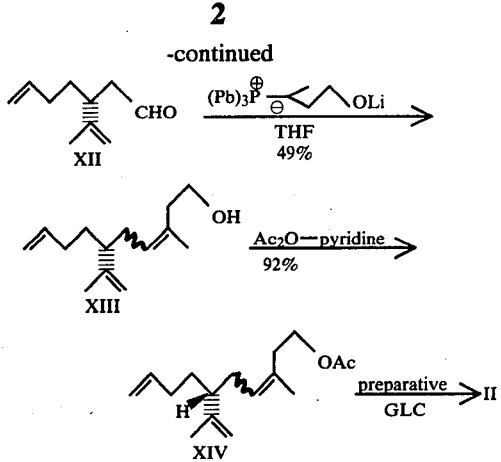

(S)-(+)-Carvone (III) is converted to the epoxide IV with alkaline hydrogen peroxide in methanol. Treatment of IV with dilute perchloric acid in tetrahydrofuran (THF) gives a mixture from which the keto diol V crystallizes. Oxidation of V with 2 equivalents of lead tetraacetate in ethanol-benzene gives directly a mixture of the diastereomeric lactones VI which are converted to the acetal ester VII with triethyl orthoformate in ethanol. Lithium aluminum hydride reduction of VII gives the alcohol acetal VIII which on reaction with p-toluenesulfonyl chloride in pyridine gives the acetal tosylate IX. The tosylate is then converted to the bromo acetal X with NaBr in hexamethylphosphoric triamide (HMPT) and reaction with vinyl lithium in THF gives the diene acetal XI. Hydrolysis of the acetal produces the diene aldehyde XII. This diene aldehyde is then reacted with the ylide generated from the corresponding 3-hydroxy-1-methylpropyltriphenylphosphonium salt to give the triene alcohols XIII. GLC analysis indicates that the Z and E isomers are formed in the Wittig reaction in a ratio of 52:48, respectively. Acetylation of XIII with acetic anhydride in pyridine gives the corresponding triene acetate XIV.

Separation of the R,Z and R,E isomers of XIV is obtained by preparative GLC separation of the mixture. The optical purity of the synthetic R and S isomers of II was determined by the following outlined technique:

Thus, the R diene aldehyde XII was oxidized with excess Jones reagent to give the corresponding acid, XV. This acid was then converted to the acid chloride (SOCL$_2$, ether, catalytic dimethylformamide), which on treatment with (R)-(+)-1-(1-naphthyl)ethylamine gave the amide XVI. Similarly, the corresponding diastereomer was prepared from the S isomer of XV and (R)-(+)-1-(1-naphthyl)ethylamine. These diastereomeric amides were completely resolved by high performance liquid chromatography (HPLC) (22×0.46 cm Zorbax-SIL, DuPont, eluted with water-saturated 10% ethyl acetate in pentane at 1.8 ml/min). From such a HPLC analysis the percentage optical purity of XVI [and hence of (R)-XIV and also of the synthetic (R,Z)-isomer II)] was shown to be 98.4%. In a like manner the S isomers of II were shown to be of 99.0% optical purity.

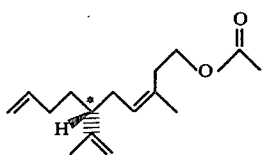

The spectrum of AII (CS$_2$; 300 MHz) is consistent with structure II with δ values as follows: 5.71 (1H, m, "J"=7,10,16 Hz [t,d,d, respectively]) 4.92 (1H, d, "J"=16 Hz), and 4.87 (1H, d, "J"=10 Hz) [$\underline{H}_2C$=C$\underline{H}$-CH$_2$—]; 5.12 (1H, t, "J"=6 Hz) [R$_2$C=C$\underline{H}$-CH$_2$—]; 4.7 (1H, s) and 4.64 (1H, s) [R$_2$C=C$\underline{H}_2$] 3.95 (2H, t, J=7.5 Hz) and 1.92 (3H, s)

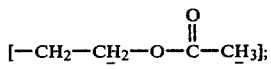

2.27 (2H, t, J=7 Hz)

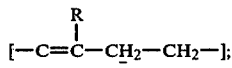

1.9–2.1 (5H, m, allylic); 1.69 (3H, s) and 1.60 (3H, s)

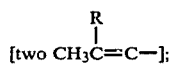

and 1.39 ppm (2H, m).

The following examples are provided to illustrate the practice of the present invention. Temperature is given in Centigrade. TLC denotes thin layer chromatography and GLC denotes gas liquid chromatography.

EXAMPLE 1

To 100 g (0.67 mol) d-carvone (III) in 600 ml methanol at 10° was added 170 ml (2 mol) 30% H$_2$O$_2$ and then 55 ml 6 N NaOH slowly (0.33 mol), maintaining the temperature in the range 10°-20°, with dry-ice bath. After about 3 hours, the reaction was poured into about 800 ml water and extracted with ether (3X 300 ml). The combined ether fractions were washed with saturated NaCl, dried over calcium sulfate and rotoevaporated to give the epoxide IV, b.p. 76°-78°.

A mixture of 80.0 g of the above epoxide, 1500 ml THF, 1100 ml water and 100 ml 7% HClO$_4$, under nitrogen, was raised to temperature of 60°-65° and then 700 ml THF was added. After about 20 hours, 50 ml 7% HClO$_4$ and 400 ml water were added. After 55 hours, the reaction was rotoevaporated to remove most of the THF. The residue was poured into ether and sat. NaCl solution. The organic phase was washed with sat. sodium bicarbonate and sat. NaCl, dried over calcium sulfate and solvent removed. The residue was stirred with 100 ml hexane and 70 ml ether and then filtered. The solid was washed with additional hexane/ether (10/7) and dried under cacuum to give the keto diol V, m.p. 104°-107°.

To 20.0 g (0.109 mol) diol V, 350 ml benzene and 150 ml ethanol, cooled in an ice-bath, was added 120 g of 85% lead tetraacetate (0.23 mol) over about 20 minutes with stirring. After about 2 hours, the reaction mixture was filtered and ether added to the filtrate, which was then washed with sodium sulfite solution, 2 N sodium carbonate and sat. NaCl, dried over calcium sulfate and solvent evaporated to give the lactones VI. [IR (CCl$_4$) 3080 (C=CH$_2$), 1760 cm$^{-1}$ (C=O); NMR (CDCl$_3$,δ) 5.35 (m 1H), 4.83 (br s, 2H), 1.77 (br s, 3H), and 1.23 ppm (t, 3H, J=7 Hz)].

To 19.0 g (0.103 mol) lactone VI and 150 ml ethanol, under nitrogen, was added 19.0 g (0.128 mol) triethylorthoformate and 0.4 g p-toluenesulfonic acid. After about 22 hours, the mixture was concentrated by evaporation and poured into ether. The organic phase was washed with sat. sodium bicarbonate and sat. NaCl, dried over calcium sulfate and rotoevaporated to yield the acetal ester VII. IR (CCl$_4$) 3075 (H$_2$C=C), 1740 cm$^{-1}$ (C=O) NMR (CDCl$_3$,δ) 4.80 (br s, 2H), 4.45 (t, 1H, J=6 Hz), and 1.70 ppm (br s, 3H).

To 25.0 g (0.097 mol) acetal ester VII and 300 ml dry THF, at 0° under nitrogen, was added 58 ml 70% sodium bis(methoxyethoxy)aluminum hydride (40.4 g hydride, 0.2 mol). After several hours, the reaction was quenched by addition of water and poured into ether and water. The aqueous phase was back extracted with chloroform. The combined organic fractions were washed with sat. NaCl, dried over calcium sulfate and solvent removed under vacuum to give alcohol acetal VIII. IR (CCl$_4$) 3630 and 3490 cm$^{-1}$ (OH); NMR (CDCl$_3$, δ) 4.82 (br s, 2H), 4.47 (t, 1H, J=6 Hz), 1.68 (s, 3H), and 1.20 ppm (t, 6H, J=7 Hz).

EXAMPLE 2

A mixture of 6.7 g (35 mmol) p-toluenesulfonyl chloride, 20 ml dry pyridine, at 0° under nitrogen, and 5.0 g (23 mmol) of alcohol acetal VIII was stirred for about 16 hours. A small amount of ice was added and after stirring, poured into ether and water. The organic phase was washed with sat. CuSO$_4$ and sat. NaCl, dried over calcium sulfa and evaporated to give acetal tosylate IX. NMR (CDCl$_3$,δ) 4.40 (t, 1H, J=5.5 Hz), 3.98 (t, 2H, J=6.5 Hz), 2.47 (s, 3H), and 1.18 ppm (t, 6H, J=7 Hz).

To 7.6 g (20.5 mmol) acetal tosylate IX and 30 ml dry HMPT, at room temperature under nitrogen, was added 3.1 g (30 mmol) sodium bromide. The reaction was stirred about 16 hours and poured into hexane/water. The aqueous phase was back extracted with hexane. The combined organic fractions were washed with water, dried over calcium sulfate and solvent evaporated to yield bromide X. Five grams (18 mmol) of the bromide in 15 ml THF was slowly added to a solution, at −20° under nitrogen, of 7 ml (21 mmol) 3 M vinyl lithium in THF and 40 ml THF. After 30 min. the cooling bath was removed and the reaction stirred at room temperature for 7 hours. A small amount of water was added and the reaction poured into ether/water. The aqueous phase was back-extracted with ether. The combined ether fractions were washed with sat. NaCl, dried over calcium sulfate and solvent evaporated to yield diene acetal XI. NMR (CDCl$_3$,δ) 4.43 (t, 1H, J=6 Hz), 1.62 (d, 3H, J=1 Hz), and 1.18 ppm (t, 6H, J=7 Hz).

EXAMPLE 3

A mixture of 1.39 g (6.15 mmol) diene acetal XI, 40 ml acetone, 20 ml water and 150 ml toluenesulfonic acid was heated at 45° for 5 hours. The reaction was poured into sat. sodium bicarbonate and ether. The aqueous phase was back-extracted with ether and the combined ether phases were washed with sat. NaCl, dried over calcium sulfate, and solvent evaporated to yield the diene aldehyde XII. IR (CCl$_4$) 3080 (H$_2$C=C), 1730 cm$^{-1}$ (C=O); NMR (CDCl$_3$,δ) 9.75 (t, 1H, J=2 Hz) and 1.67 ppm (br s, 3H).

To 2.6 g (6.5 mmol) 3-hydroxypropyltriphenylphosphonium bromide in 30 ml dry THF at 0° under nitrogen was added 8.05 ml (12.9 mmol) 1.60 M n-butyllithium in hexane. After about 30 min, 920 mg (6.5 mmol) methyl iodide was added. The reaction mixture was stirred for about 30 min and 4.0 ml (6.4 mmol) 1.60 M n-butyllithium in hexane was added. After 15 min, diene aldehyde (0.80 g) XII in THF was added. After 2 hours, several ml of water was added and then the reaction poured into ether/water. The aqueous phase was back-extracted with ether. The combined ether fractions were washed with sat. NaCl, dried over calcium sulfate and solvent evaporated. The residue was applied to thin layer chromatography plates, eluted with 17% ethyl acetate/hexane, and the alcohol band removed to yield the triene alcohols XIII. IR (CCl$_4$) 3625 and 3540 (OH), 3075 cm$^{-1}$ (H$_2$C=C); NMR (CDCl$_3$,δ) 3.67 (t, J=7 Hz), 3.61 (t, J=6.5 Hz), and 1.62 and 1.70 ppm (both br s, 6H).

A mixture of the triene alcohols XIII (500 mg, 2.42 mmol), 3 ml pyridine and 0.7 ml acetic anhydride, under nitrogen, was heated to 60° for 3 hours. Then a small amount of ice was added followed by stirring for 30 minutes. The reaction was poured into ether and sat. CuSO$_4$ solution. The organic phase was washed with CuSO$_4$ solution, sodium carbonate and sat. NaCl, dried over calcium sulfate and solvent evaporated to give triene acetates XIV. IR (CCl$_4$) 3080 (C=CH$_2$), 1745 cm$^{-1}$ (C=O); NMR (CDCl$_3$,δ) 4.10 and 4.13 (two t, 2H, J=7 Hz), 2.03 (s, 3H), and 1.62 and 1.70 ppm (both br s, 6H).

What is claimed is:
1. The compound, 3-isopropenyl-6-heptenoic acid.
2. The 3R-enantiomer of the compound of claim 1.